United States Patent [19]

Takaya et al.

[11] Patent Number: 5,306,834
[45] Date of Patent: Apr. 26, 1994

[54] PROCESS FOR PREPARING OPTICALLY ACTIVE 4-METHYL-2-OXETANONE

[75] Inventors: Hidemasa Takaya, Shiga; Tetsuo Ohta, Kyoto; Hidenori Kumobayashi, Tokyo, all of Japan

[73] Assignee: Takasago International Corporation, Tokyo, Japan

[21] Appl. No.: 92,446

[22] Filed: Jul. 14, 1993

[30] Foreign Application Priority Data

Jul. 16, 1992 [JP] Japan .................................. 4-210683
Jun. 30, 1993 [JP] Japan .................................. 5-183490

[51] Int. Cl.$^5$ .......................................... C07D 305/12
[52] U.S. Cl. ...................................................... 549/263
[58] Field of Search .......................................... 549/263

[56] References Cited

U.S. PATENT DOCUMENTS

| 2,763,664 | 9/1956 | Sixt ................................ 549/328 |
| 4,691,037 | 9/1987 | Yoshikawa et al. .................. 556/18 |
| 4,739,084 | 4/1988 | Takaya et al. ...................... 556/21 |
| 4,739,085 | 4/1988 | Takaya et al. ...................... 556/21 |
| 4,764,629 | 8/1988 | Sayo et al. ......................... 556/23 |
| 4,766,225 | 8/1988 | Sayo et al. ......................... 556/16 |
| 4,766,227 | 8/1988 | Sayo et al. ......................... 556/21 |
| 4,994,590 | 2/1991 | Takaya et al. ...................... 556/21 |
| 5,012,002 | 4/1991 | Kumobayashi et al. ............... 568/17 |
| 5,021,593 | 6/1991 | Nohira et al. ...................... 556/20 |

FOREIGN PATENT DOCUMENTS

| 0444930 | 9/1991 | European Pat. Off. . |
| 0466405 | 1/1992 | European Pat. Off. . |
| 0479542 | 4/1992 | European Pat. Off. . |
| 47-25065 | 7/1972 | Japan . |
| 64-68386 | 3/1989 | Japan . |
| 5-111639 | 5/1993 | Japan . |

OTHER PUBLICATIONS

J. Reid Shelton, et al, *Polymer Letters*, vol. 9, pp. 173-178 (1971).
T. Sato, et al, *Tetrahedron Lett.*, vol. 21, pp. 3377-3380 (1980).
A. Griesbeck, et al, *Helv. Chim. Acta*, vol. 70, pp. 1320-1325 (1987).
R. Breitschuh, et al, *Chimia*, vol. 44, pp. 216-218 (1990).
Y. Zhang, et al, *Macromolecules*, vol. 23, pp. 3206-3212 (1990).
R. Schmid et al, *Helv. Chim. Acta*, vol. 74, pp. 370-389 (1991).
R. Schmid, et al, *Helv. Chim. Acta*, vol. 71, pp. 897-929 (1988).
N. Yamamoto et al, *Chem. Pharm. Bull.*, vol. 39, No. 4, pp. 1085-1087 (1991).
T. Ikariya, et al, *J. Chem. Soc., Chem. Commun.*, pp. 922-924 (1985).
J. P. Genet, et al, *Tetrahedron:Asymmetry*, vol. 2, No. 7, pp. 555-567 (1991).

*Primary Examiner*—Bernard Dentz
*Attorney, Agent, or Firm*—Sughrue, Mion, Zinn, Macpeak & Seas

[57] ABSTRACT

A process for preparing optically active 4-methyl-2-oxetanone which comprises asymmetrically hydrogenating 4-methylene-2-oxetanone in the presence of a ruthenium-optically active phosphine complex. Optically active 4-methyl-2-oxetanone can easily and economically be obtained at high optical purity.

7 Claims, No Drawings

PROCESS FOR PREPARING OPTICALLY ACTIVE 4-METHYL-2-OXETANONE

FIELD OF THE INVENTION

This invention relates to a process for preparing optically active 4-methyl-2-oxetanone useful as an intermediate in synthesizing organic compounds, such as polymers, medicines, and liquid crystal materials.

BACKGROUND OF THE INVENTION

4-Methyl-2-oxetanone, also called β-butyrolactone or β-methyl-β-propiolactone, has been prepared by reaction between ketene and acetaldehyde as disclosed in JP-B-47-25065 (the term "JP-B" as used herein means an "examined published Japanese patent application") or hydrogenation of 4-methylene-2-oxetanone, also called diketene, in the presence of palladium black as disclosed in U.S. Pat. No. 2,763,644.

While 4-methyl-2-oxetanone has been used, for example, as a starting material of polymers (see Yuya Yamashita, et al., *KOGYO KAGAKU ZASSHI*, Vol. 66, No. 1, pp. 110-115 (1963)), attention is now given to the usefulness of its optically active form as reported by N. Tanahashi, et al., *Macromolecules*, Vol. 24, pp. 5732-5733 (1991).

The above-mentioned conventional processes only produce a racemic modification of 4-methyl-2-oxetanone. Processes for producing optically active 4-methyl-2-oxetanone which have been proposed to date include:

(1) a process comprising optically resolving 3-bromobutyric acid, which is obtained by addition of hydrobromic acid to crotonic acid, by using optically active naphthylethylamine followed by cyclization (see J. Reid Shelton, et al., Polymer Letters, Vol. 9, pp. 173-178 (1971) and T. Sato, et al., *Tetrahedron Lett.*, Vol. 21, pp. 3377-3380 (1980)), 2) a process comprising reacting optically active 3-hydroxybutyric acid with triethylorthoacetic acid to obtain optically active 2-ethoxy-2,6-dimethyl-1,3-dioxan-4-one, which is then thermally decomposed (see A. Griesbeck, et al., *Helv. Chim. Acta*, Vol. 70, pp. 1320-1325 (1987) and R. Breitschuh, et al., *Chimia*, Vol. 44, pp. 216-218 (1990)), and 3) a process comprising reacting an optically active 3-hydroxybutyric ester with methanesulfonyl chloride to mesylate the hydroxyl group, hydrolyzing the resulting ester, followed by condensation and cyclization using sodium hydrogencarbonate (see Y. Zhang, et al., *Macromolecules*, Vol. 23, pp. 3206-3212 (1990)).

These known processes for preparing optically active 4-methyl-2-oxetanone have their several disadvantages as follows.

Process (1) not only requires a special optically active amine as a resolving agent in an equimolar amount with the starting compound but by-produces an unnecessary enantiomer in an equimolar amount with the purposed isomer. Therefore, this process involves much waste and is uneconomical.

Processes (2) and (3) encounter difficulty in synthesizing the starting compound, i.e., optically active 3-hydroxybutyric acid or an ester thereof. That is, the synthesis of these compounds involves many steps and complicated operation, such as thermal decomposition of an optically active poly-3-hydroxybutyric ester produced by a microorganism, or subjecting racemic 4-methyl-2-oxetanone to alcoholysis to once obtain an acetoacetic ester, which is then asymmetrically reduced.

Hence, it has been keenly demanded to develop a process for preparing optically active 4-methyl-2-oxetanone which is easy to carry out and economically advantageous.

SUMMARY OF THE INVENTION

In the light of the above-described situation, the present inventors have conducted extensive investigations. As a result, it has now been found that optically active 4-methyl-2-oxetanone can be prepared with not only ease and economical advantages but high optical purity by asymmetrical hydrogenation of easily available 4-methylene-2-oxetanone in the presence of a relatively cheap ruthenium-optically active phosphine complex as a catalyst according to the following reaction scheme:

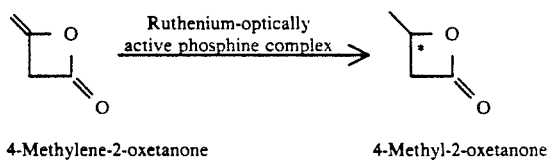

4-Methylene-2-oxetanone      4-Methyl-2-oxetanone wherein * indicates an asymmetric carbon atom.

The present invention provides a process for preparing optically active 4-methyl-2-oxetanone which comprises asymmetrically hydrogenating 4-methylene-2-oxetanone in the presence of a ruthenium-optically active phosphine complex as a catalyst.

DETAILED DESCRIPTION OF THE INVENTION

The starting compound, 4-methylene-2-oxetanone, which can be used in the process of this invention, can easily be prepared by thermal decomposition of acetic acid or acetic anhydride according to the process described in R. J. Clemens, et al., *Chem. Rev*, Vol. 86, pp. 241-318 (1986).

Specific examples of the ruthenium-optically active phosphine complexes which can be used as a catalyst include:

(1) $Ru_xH_yCl_z(CBP)_2(A)_w$ wherein CBP represents $R^1$-BINAP or BIPHEP, wherein $R^1$-BINAP represents a tertiary phosphine represented by formula:

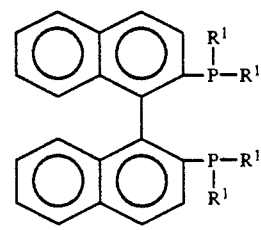

wherein $R^1$ represents an aryl group or a cycloalkyl group having from 3 to 8 carbon atoms; and
BIPHEP represents a tertiary phosphine represented by formula

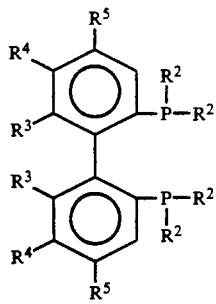

wherein $R^2$ represents an aryl group or a cyclohexyl group; $R^3$ represents a methyl group or a methoxy group; $R^4$ represents a hydrogen atom, a methyl group or a methoxy group; $R^5$ represents a hydrogen atom, a methyl group, a methoxy group or a di-lower alkyl-substituted amino group; and $R^3$, $R^4$ and their adjacent phenyl group may together form an octahydronaphthyl group;
A represents a tertiary amine; y represents 0 or 1; when y is 0, x is 2, z is 4, and w is 1; and when y is 1, x is 1, z is 1, and w is 0.

(2) $[RuH_m(CBP)_n]T_p$ wherein CBP is as defined above; T represents $ClO_4$, $BF_4$, or $PF_6$; when m is 0, n represents 1, and p represents 2; and when m is 1, n represents 2, and p represents 1.

(3) $[RuX_a(Q)_b(CBP)]L_c$ wherein CBP is as defined above; X represents a halogen atom; Q represents substituted or unsubstituted benzene or acetonitrile; L represents a halogen atom, $ClO_4$, $PF_6$, $BF_4$ or $BPh_4$ (wherein Ph represents a phenyl group, hereinafter the same); when Q is substituted or unsubstituted benzene, a, b, and c each represent 1; when Q is acetonitrile, a is 0, b is 4, and c is 2, or a is 1, b is 2, and c is 1; and when Q is p-cymene which is a substituted benzene and X and L both are an iodine atom, a is 1, b is 1, and c is 1 or 3.

(4) $Ru(CBP)J_2$ wherein CBP is as defined above; and J represents a chlorine atom, a bromine atom or $O_2CR^6$, wherein $R^6$ represents a lower alkyl group or a halogen-substituted lower alkyl group.

(5) $RuG_2(CBP)$ wherein CBP is as defined above; and G represents an allyl group or a methallyl group.

Of the above complexes (1) to (5), when CBP is $R^1$-BINAP, the aryl group represented by $R^1$ represents an unsubstituted phenyl group or a substituted phenyl group such as p-substituted phenyl, m-substituted phenyl, and m-disubstituted phenyl. The substituents for the substituted phenyl group include a straight chain or branched alkyl group having from 1 to 4 carbon atoms such as methyl and t-butyl and a methoxy group. Of the cycloalkyl groups having from 3 to 8 carbon atoms represented by $R^1$, a cyclopentyl group and a cyclohexyl group are particularly preferred.

Specific examples of the tertiary phosphines represented by $R^1$-BINAP include:

(a) 2,2'-bis(diphenylphosphino)-1,1'-binaphthyl (hereinafter referred to as "BINAP");

(b) 2,2'-bis(di-p-tolylphosphino)-1,1'-binaphthyl (hereinafter referred to as "Tol-BINAP");

(c) 2,2'-bis(di-p-t-butylphenylphosphino)-1,1'-binaphthyl (hereinafter referred to as "t-Bu-BINAP");

(d) 2,2'-bis(di-m-tolylphosphino)-1,1'-binaphthyl (hereinafter referred to as "m-Tol-BINAP");

(e) 2,2'-bis[di-(3,5-dimethylphenyl)phosphino]-1,1'-binaphthyl (hereinafter referred to as "DM-BINAP");

(f) 2,2'-bis(di-p-methoxyphenylphosphino)-1,1'-binaphthyl binaphthyl (hereinafter referred to as "Methoxy-BINAP");

(g) 2,2'-bis(dicyclopentylphosphino)-1,1'-binaphthyl (hereinafter referred to as "CpBINAP"); and (h) 2,2'-bis(dicyclohexylphosphino)-1,1'-binaphthyl (hereinafter referred to as "CyBINAP").

These tertiary phosphines can be prepared by the methods as described in U.S. Pat. Nos. 4,691,037 and 5,012,002, EP-A-0444930, JP-A-1-68386 (the term "JP-A" as used herein means an "unexamined published Japanese patent application"), and EP-A-0466405.

Of the above complexes (1) to (5), when CBP is BIPHEP, the aryl group represented by $R^2$ represents an unsubstituted phenyl group or a substituted phenyl group such as p-substituted phenyl, m-substituted phenyl, and m-disubstituted phenyl. The substituents for the substituted phenyl group include a straight chain or branched alkyl group having from 1 to 4 carbon atoms such as methyl and t-butyl and a methoxy group. Further, the "lower alkyl" of the dilower alkyl-substituted amino group represented by $R^5$ means a straight chain or branched alkyl group having from 1 to 4 carbon atoms.

Specific examples of the tertiary phosphines represented by BIPHEP include:

(i) 2,2'-dimethyl-6,6'-bis(diphenylphosphino)-1,1'-biphenyl (hereinafter referred to as "BIPHEMP");

(j) 2,2'-dimethyl-6,6'-bis(dicyclohexylphosphino)-1,1'-biphenyl (hereinafter referred to as "BICHEP");

(k) 2,2'-bis(diphenylphosphino)-5,5',6,6',7,7',8,8'-octahydro-1,1'-binaphthyl (hereinafter referred to as "OcHBINAP");

(l) 2,2'-dimethyl-4,4'-bis(dimethylamino)-6,6'-bis(diphenylphosphino)-1,1'-biphenyl;

(m) 2,2',4,4'-tetramethyl-6,6'-bis(diphenylphosphino)-1,1'-biphenyl;

(n) 2,2'-dimethoxy-6,6'-bis(diphenylphosphino)-1,1'-biphenyl;

(o) 2,2',3,3'-tetramethoxy-6,6'- bis(diphenylphosphino)-1,1'-biphenyl;

(p) 2,2',4,4'-tetramethyl-3,3'-dimethoxy-6,6'-bis(diphenylphosphino)-1,1'-biphenyl;

(q) 2,2'-dimethyl-6,6'-bis(di-p-tolylphosphino)-1,1'-biphenyl;

(r) 2,2'-dimethyl-6,6'-bis(di-p-tertbutylphenylphosphino)-1,1'-biphenyl; and (s) 2,2',4,4'-tetramethyl-3,3'-dimethoxy-6,6'-bis(di-p-methoxyphenylphosphino)-1,1'-biphenyl.

These tertiary phosphines can be prepared by the methods as described in U.S. Pat. Nos. 4,764,629 and 5,021,593, EP-A-0479542, R. Schmid et al., *Helv. Chim. Acta*, Vol. 74, pp. 370–389 (1991), R. Schmid et al., *Helv. Chim. Acta*, Vol. 71, pp. 897–929 (1988), and N. Yamamoto et al., *Chem. Pharm. Bull.*, Vol. 39, No. 4, pp. 1085–1087 (1991).

Of the ruthenium-optically active phosphine complexes (1) (hereinafter referred to optically active complexes 1), those wherein CBP is R:-BINAP can be obtained by the processes disclosed in T. Ikariya, et al., *J. Chem. Soc., Chem. Commun.*, pp. 922–924 (1985) and U.S. Pat. No. 4,691,037. More specifically, these complexes can be prepared by reacting ruthenium chloride and cycloocta-1,5-diene (hereinafter abbreviated as COD) in ethanol to obtain $[RuX_2(COD)]_q$ (q represents a natural number) and reacting the resulting product with $R^1$-BINAP in a solvent, e.g., toluene or ethanol, in the presence of a tertiary amine represented by A, preferably triethylamine, under heating.

Specific examples of the tertiary amine include triethylamine, tributylamine, ethyldiisopropylamine, 1,8-bis(-dimethylamino)naphthalene, dimethylaniline, pyridine, N-methylpiperidine, etc., and triethylamine is particularly preferred.

Optically active complexes 1 wherein CBP is BIPHEP can be obtained by the process disclosed in U.S. Pat. No. 4,764,629.

Specific examples of optically active complexes 1 are shown below:

1-1. $Ru_2Cl_4(BINAP)_2NE_3$
1-2. $Ru_2Cl_4(Tol-BINAP)_2NEt_3$
1-3. $Ru_2Cl_4(t-Bu-BINAP)_2NEt_3$
1-4. $Ru_2Cl_4(m-Tol-BINAP)_2NEt_3$
1-5. $Ru_2Cl_4(DM-BINAP)_2NEt_3$
1-6. $Ru_2Cl_4(Methoxy-BINAP)_2NEt_3$
1-7. $Ru_2Cl_4(CpBINAP)_2NEt_3$
1-8. $Ru_2Cl_4(CyBINAP)_2NEt_3$
1-9. $RuHCl(BINAP)_2$
1-10. $RuHCl(Tol-BINAP)_2$
1-11. $RuHCl(DM-BINAP)_2$
1-12. $Ru_2Cl_4(BIPHEMP)_2NEt_3$
1-13. $RuHCl(BIPHEMP)_2$
1-14. $Ru_2Cl_4(BICHEP)_2NEt_3$
1-15. $RuHCl(BICHEP)_2$
1-16. $Ru_2Cl_4(OcHBINAP)_2NEt_3$ The ruthenium-optically active phosphine complexes (2) (hereinafter referred to as optically active complexes 2) can be prepared by the processes disclosed, e.g., in U.S. Pat. Nos. 4,739,085 and 4,766,227.

That is, those of the complexes 2 wherein m is 0, n is 1, and p is 2 are prepared by reacting $Ru_2Cl_4(CBP)_2NEt_3$, one of optically active complexes 1, with a salt represented by MT (wherein T is as defined above; and M represents Na, K, Li, Mg or Ag; hereinafter the same) in the presence of an correlated transfer catalyst selected from a quaternary ammonium salt and a quaternary phosphonium salt. Those wherein m is 1, n is 2, and p is 1 are prepared by reacting $RuHCl(CBP)_2$, one of optically active complexes 1, with a salt represented by MT in the presence of the above-mentioned correlated transfer catalyst.

Specific examples of optically active complexes 2 are shown below.

2-1. $[Ru(BINAP)](ClO_4)_2$
2-2. $[Ru(Tol-BINAP)](PF_6)_2$
2-3. $[Ru(BINAP)](BF_4)_2$
2-4. $[Ru(Methoxy-BINAP)](BF_4)_2$
2-5. $[RuH(BINAP)_2]ClO_4$
2-6. $[RuH(t-Bu-BINAP)_2]PF_6$
2-7. $[RuH(Tol-BINAP)_2]BF_4$
2-8. $[RuH(BIPHEMP)_2]ClO_4$ The ruthenium-optically active phosphine complexes (3) (hereinafter referred to as optically active complexes 3) are obtained by the process disclosed in, e.g., U.S. Pat. No. 4,994,590.

For example, those wherein Q is substituted or unsubstituted benzene; and X and L both represent a halogen atom are prepared by reacting $[RuX_2(Q^1)]_2$ (wherein X is as defined above; and $Q^1$ represents a substituted or unsubstituted benzene; hereinafter the same) and CBP in an appropriate solvent such as methanol, ethanol, benzene, methylene chloride, and the mixture thereof.

Those wherein Q is p-cymene; X and L both represent an iodine atom; a is 0; b is 0; and c is 3 are prepared by reacting a compound of [RuI(p-cymene)(CBP)]I with iodine in an appropriate solvent such as methanol at a temperature of from 15° to 30° C. for 1 to 5 hours, as disclosed in JP-A-5-111639.

Those wherein Q is substituted or unsubstituted benzene; and L is $ClO_4$, $PF_6$, $BF_4$ or $BPh_4$ are prepared by reacting $[RuX(Q^1)(CBP)]$ resulted above with a salt represented by $ML^1$ (wherein M is as defined above; and $L^1$ represents $ClO_4$, $PF_6$, $BF_4$ or $BPh_4$).

The substituted benzene as represented by Q include benzene substituted with a lower alkyl group, a lower alkoxy group, a lower alkoxycarbonyl group, a halogen atom, etc. The term "lower" as used herein means a straight chain or branched chain having from 1 to 4 carbon atoms. Specific examples of the substituted benzene are toluene, xylene, trimethylbenzene, hexamethylbenzene, ethylbenzene, t-butylbenzene, p-cymene, cumene, anisole, methylanisole, methyl benzoate, methyl methylbenzoate, methyl chlorobenzoate, chlorobenzene, dichlorobenzene, trichlorobenzene, bromobenzene, and fluorobenzene.

Optically active complexes 3 wherein Q is acetonitrile, a is 1, b is 2, and c is 1 are obtained by, for example, heating $[RuX(Q^1)(CBP)]X$ as dissolved in acetonitrile at about 50° C.

The complexes 3 wherein Q is acetonitrile, a is 0, b is 4, and c is 2 are prepared by heating $[RuX(Q^1)(CBP)]X$ as dissolved in a mixed solvent of acetonitrile and any other appropriate solvent such as methanol, ethanol, acetone, and methylene chloride at a temperature of from about 25° to 50° C.

Specific examples of optically active complexes 3 are shown below.

3-1. [RuCl(benzene)(BINAP)]Cl
3-2. [RuCl(benzene)(Tol-BINAP)]Cl
3-3. [RuBr(benzene)(BINAP)]Br
3-4. [RuI(p-cymene)(BINAP)]I
3-5. [RuI(p-cymene)(m-Tol-BINAP)]I
3-6. $[RuI(p-cymene)(BINAP)]I_3$
3-7. $[RuI(p-cymene)(Tol-BINAP)]I_3$
3-8. $[RuI(p-cymene)(DM-BINAP)]I_3$
3-9. [RuCl(methyl benzoate)(BINAP)]Cl
3-10. $[RuCl(benzene)(BINAP)]ClO_4$
3-11. $[RuCl(benzene)(t-Bu-BINAP)ClO_4$
3-12. $[RuCl(benzene)(BINAP)]PF_6$
3-13. $[RuCl(benzene)(BINAP)]BF_4$
3-14. $[RuCl(benzene)(BINAP)BPh_4$
3-15. $[Ru(acetonitrile)_4(BINAP)](BF_4)_2$
3-16. $[RuCl(acetonitrile)_2(BINAP)]Cl$
3-17. [RuBr(benzene](3,5-dimethyl-BINAP)]Br
3-18. [RuCl(benzene)(BIPHEMP)]Cl
3-19. [RuI(p-cymene)(BIPHEMP)]Cl
3-20. [RuI(p-cymene)(BIPHEMP)]I
3-21. [RuI(p-cymene)(OcHBINAP)]I Of the ruthenium-optically active phosphine complexes (4) (hereinafter referred to as optically active complexes 4), those wherein J is a chlorine atom or a bromine atom can be obtained, for example, by the process described in J. P. Genet, et al., *Tetrahedron-*

*Asymmetry*, Vol. 2, No. 7, pp. 555–567 (1991). More specifically, they are prepared by reacting CBP as dissolved in an appropriate solvent such as methylene chloride, toluene, and acetone with a methanolic solution of an acid represented by HJ (wherein J is as defined above).

Optically active complexes 4 wherein J is $O_2CR^6$ are prepared, for example, by reacting $Ru_2Cl_4(CBP)_2NEt_3$, one of optically active complexes 1, with a carboxylic acid salt corresponding to the moiety $O_2CR^6$ in an alcohol solvent as disclosed in U.S. Pat. Nos. 4,739,084 and 4,766,225. The term "lower alkyl group" as for $R^6$ means a straight chain or branched alkyl group having from 1 to 4 carbon atoms, and the term "halogen-substituted lower alkyl group" as for $R^6$ means a straight chain or branched alkyl group having from 1 to 4 carbon atoms and one or more halogen atoms. Specific examples of the halogen-substituted alkyl group include monochloromethyl, dichloromethyl, trichloromethyl, and trifluoromethyl groups. The compounds wherein $R^6$ is a trifluoromethyl group can be prepared by, for example, reacting the resulting $Ru(CBP)(O_2CCH_3)_2$ with trifluoroacetic acid.

Specific examples of optically active complexes 4 are shown below.
4-1. $Ru(BINAP)Cl_2$
4-2. $Ru(BINAP)Br_2$
4-3. $Ru(Tol-BINAP)Br_2$
4-4. $Ru(t-Bu-BINAP)Br_2$
4-5. $Ru(BINAP)(O_2CCH_3)_2$
4-6. $Ru(Tol-BINAP)(O_2CCH_3)_2$
4-7. $Ru(BINAP)(O_2CCF_3)_2$
4-8. $Ru(3,5-dimethyl-BINAP)Cl_2$
4-9. $Ru(BIPHEMP)Br_2$
4-10. $Ru(BICHEP)(O_2CCH_3)_2$
4-11. $Ru(OcHBINAP)(O_2CCH_3)_2$ The ruthenium-optically active phosphine complexes (5) (hereinafter referred to as optically active complexes 5) can also be prepared by the process of J. P. Genet, et al. (*Tetrahedron:Asymmetry*, Vol. 2, No. 7, pp. 555–567 (1991)). More specifically, they are obtained by heating $RuG_2(COD)$ (wherein G is as defined above) and CBP in a solvent, e.g., hexane, in an argon atmosphere at about 50° C.

Specific examples of optically active complexes 5 are shown below.
5-1. $Ru(C_3H_5)_2(BINAP)$ (wherein $C_3H_5$ is an allyl group, hereinafter the same)
5-2. $Ru(C_3H_5)_2(t-Bu-BINAP)$
5-3. $Ru(C_4H_7)_2(BINAP)$ (wherein $C_4H_7$ is a methallyl group, hereinafter the same)
5-4. $Ru(C_4H_7)_2(Tol-BINAP)$
5-5. $Ru(C_3H_5)_2(3,5-dimethyl-BINAP)$
5-6. $Ru(C_4H_7)_2(BIPHEMP)$ The ruthenium-optically active phosphine complexes which can be used in the present invention are not particularly limited to those of the above complexes 1 to 5, and, for example, the following ruthenium-optically active phosphine complexes (6) and (7) can also be used.

(6) $[Ru(CBP)ZCl_q]_r(R^7)_s$
wherein CBP is as defined above; Z represents Zn, Al, Ti or Sn; $R^7$ represents $NEt_3$ or $O_2CCH_3$; and when $R^7$ is $NEt_3$, r is 2, s is 1, and q is 4 when Z is Zn, or q is 5 when Z is Al, or q is 6 when Z is Ti or Sn; and when $R^7$ is $O_2CCH_3$, r is 1, s is 2, and q is 2 when Z is Zn, or q is 3 when Z is Al, or q is 4 when Z is Ti or Sn.

The ruthenium-optically active phosphine complexes (6) (hereinafter referred to as optically active complexes 6) are obtained by the process as disclosed in, e.g., U.S. Pat. No. 4,954,644, which comprises the step of reacting $Ru_2Cl_4(CBP)_2NEt_3$ which is a kind of optically active complexes 1 or $Ru(CBP)_2(O_2CCH_3)_2$ which is a kind of optically active complexes 4 with Lewis acid selected from zinc chloride, aluminum chloride, titanium tetrachloride, and tin tetrachloride in a solvent such as methylene chloride at a temperature of from 10° to 25° C. for 2 to 20 hours.

Specific examples of optically active complexes 6 are shown below.
6-1. $[Ru(BINAP)ZnCl_4]_2NEt_3$
6-2. $[Ru(BINAP)AlCl_5]_2NEt_3$
6-3. $[Ru(Tol-BINAP)AlCl_5]_2NEt_3$
6-4. $[Ru(BINAP)TiCl_6]_2NEt_3$
6-5. $[Ru(Tol-BINAP)TiCl_6]_2NEt_3$
6-6. $[Ru(BINAP)SnCl_6]_2NEt_3$
6-7. $[Ru(Tol-BINAP)SnCl_6]_2NEt_3$
6-8. $[Ru(BINAP)ZnCl_2](O_2CCH_3)_2$
6-9. $[Ru(Tol-BINAP)ZnCl_2](O_2CCH_3)_2$
6-10. $[Ru(BINAP)AlCl_3](O_2CCH_3)_2$
6-11. $[Ru(Tol-BINAP)AlCl_3](O_2CCH_3)_2$
6-12. $[Ru(BINAP)TiCl_4](O_2CCH_3)_2$
6-13. $[Ru(Tol-BINAP)TiCl_4](O_2CCH_3)_2$
6-14. $[Ru(BINAP)SnCl_4](O_2CCH_3)_2$
6-15. $[Ru(Tol-BINAP)SnCl_4](O_2CCH_3)_2$ (7) $Ru(CBP)(R^8)_t(R^9)_u$
wherein CBP is as defined above; $R^8$ and $R^9$ independently represent diketones or anionic ligands usable for general complex; provided that at least one of $R^8$ and $R^9$ represents a diketone; t represents 1 or 2; and u represents 1 when t is 1 or u represents 0 when t is 2.

The "diketone" represented by $R^8$ and $R^9$ refers to compounds of the formula;

$R^{10}-C(=O)-CHR^{11}-C(=O)-R^{12}$ wherein $R^{10}$, $R^{11}$ and $R^{12}$ independently represent hydrogen, and substituted and unsubstituted alkyl, cycloalkyl, aryl, aralkyl, alkaryl, and the like radicals.

Where such radicals are substituted, substituents can include halogen, sulfones and sulfoxides, alkoxides, carboxyl, silyl, amino, and the like.

Examples of such diketones include, but are not limited to the following: acetylacetonate (acac); 1,1,1-trifluoro-2,4-pentanedione; 1-methoxy-2,4-heptanedione; 1-methoxy-7-octene-2,4-dione; 1,1-diethoxy-2,4-pentanedione; 1,1,1-trifluoro-3,5-heptanedione; N,N-diethyl-5-methyl-2,4-dioxohexanamide; 1,1',1''-tris(2,4-pentanedione)methylsilylidyne; 1,5-bis(dimethylamino)-2,4-pentanedione and the like.

Examples of anionic ligands usable for general complex include halides such as I, Br, Cl and F, $ClO_4$, $BF_4$, $PF_6$, acetate and the like.

The ruthenium-optically active phosphine complexes (7) (hereinafter referred to as optically active complexes 7) are obtained by the process disclosed in, e.g., U.S. Pat. No. 5,144,050.

For example, those wherein $R^8$ and $R^9$ both are a diketonate are prepared by reacting a Ru(III) species such as $Ru(diketonate)_3$ with CBP in the presence of a reducing agent such as zinc dust in a suitable solvent such as ethanol.

Specific examples of optically active complexes 7 are shown below.

7-1. Ru(BINAP)(acac)$_2$
7-2. Ru(Tol-BINAP)(acac)$_2$
7-3. Ru(t-Bu-BINAP)(acac)$_2$
7-4. Ru(BINAP)(acac)(O$_2$CCH$_3$)
7-5. Ru(BINAP)(acac)(Cl)
7-6. Ru(BINAP)(acac)(Br)
7-7. Ru(BINAP)(acac)(I)
7-8. Ru(BINAP)(acac)(ClO$_4$)
7-9. Ru(BINAP)(acac)(BF$_4$)
7-10. Ru(BINAP)(acac)(PF$_6$)
7-11. Ru(BINAP)(acac)(BPh$_4$)

Each of the phosphine derivatives in optically active complexes 1 to 7 has either a (+)-form or a (−)-form while not indicated. Optically active 4-methyl-2-oxetanone having a desired absolute configuration can be obtained by choosing either of the (+)- and (−)-forms of the optically active complex.

In order to practice the present invention advantageously, it is preferred to use the ruthenium-optically active phosphine complexes prepared by mixing the ruthenium with the optically active phosphine in a molar ratio of from 1:1 to 1:0.95. In the preparation of the ruthenium-optically active phosphine complexes, normally about 1.05 to 1.2 equivalent mole of an optically active phosphine ligand is used per one equivalent mole ruthenium. In the present invention, however, polymerization of 4-methylene-2-oxetanone which is a side reaction can be prevented by controlling the amount of the optically active phosphine ligand to one equivalent mole or less of the ruthenium. Further, it is also preferred to use the optically active phosphine ligand in an amount of not less than 0.95 equivalent of the ruthenium due to economy.

In carrying out the present invention, the above-described ruthenium-optically active phosphine complex, 4-methylene-2-oxetanone, and a solvent are put in a pressure vessel in a nitrogen atmosphere, and asymmetric hydrogenation is conducted in a hydrogen atmosphere.

The ruthenium-optically active phosphine complex is usually used in an amount of from about 0.0001 to 0.01 mol, preferably about 0.0005 to 0.002 mol, per mol of 4-methylene-2-oxetanone. If the catalyst amount is less than 0.0001 mol, a sufficient catalytic action cannot be exerted. A catalyst amount exceeding 0.01 mol is bad economy.

Any of solvents usable for general asymmetric hydrogenation, except those reactive with the starting compound, such as alcohols and water, can be employed. Suitable solvents include methylene chloride, acetone, methyl ethyl ketone, methyl butyl ketone, tetrahydrofuran, 1,4-dioxane, ethyl acetate, and butyl acetate. However, the presence of acids such as acetic acid, propionic acid, etc. retards the reaction.

In order to accelerate the hydrogenation reaction and to increase the selectivity and optical purity of the product, it is preferable to add from about 0.5 to 1 equivalent of a tertiary amine based on the catalyst. Particularly, the tertiary amine should be added except for the case in which the amine-containing catalyst such as optically active phosphine complexes 1 is used. However, the addition of excess of tertiary amine is not always advantageous.

When the tertiary amine is added, the reaction is preferably effected by first putting a ruthenium-optically active phosphine complex in a pressure vessel in a nitrogen atmosphere, adding a solvent thereto to dissolve the complex, then adding a tertiary amine thereto, and, after stirring the mixture at a temperature of from room temperature to 60° C. for a period of from about 10 minutes to about 2 hours, adding 4-methylene-2-oxetanone to the mixture to conduct asymmetric hydrogenation in a hydrogen atmosphere. Examples of suitable tertiary amines to be used include triethylamine, tributylamine, diisopropylethylamine, 1,8-bis(dimethylamino)naphthalene, dimethylaniline, pyridine, and N-methylpiperidine.

The asymmetric hydrogenation reaction is usually conducted at a temperature of from room temperature to 100° C., preferably from 30° to 60° C., for a period of from about 15 to 150 hours, while varying depending on the kind of the catalyst used and other conditions. The hydrogen pressure is preferably in the range of from about 5 to 150 kg/cm$^2$, preferably from 50 to 100 kg/cm$^2$.

After completion of the reaction, the reaction product can be purified by solvent distillation, distillation, and the like to isolate optically active 4-methyl-2-oxetanone.

The present invention will now be illustrated in greater detail by way of Examples, but it should be understood that the present invention is not construed as being limited thereto.

As the ruthenium-optically active phosphine complexes used in Examples 1 to 20, those prepared by mixing ruthenium with an optically active phosphine in a molar ratio of about 1:1 were used.

EXAMPLE 1

In a 100 ml-volume stainless steel-made autoclave was charged 16.9 mg (0.01 mmol) of Ru$_2$Cl$_4$((+)-BINAP)$_2$NEt$_3$ in a nitrogen atmosphere, and 10 ml of methylene chloride was added thereto to dissolve. To the solution was added 2.6 mg (0.02 mol) of diisopropylethylamine, and the mixture was stirred at 50° C. under for 20 minutes. Then, 1.7 g (20 mmol) of 4-methylene-2-oxetanone was added thereto, followed by stirring at 50° C. under a hydrogen pressure of 50 kg/cm$^2$ for 90 hours. The resulting reaction mixture was distilled by means of a Claisen flask to obtain 1.63 g (percent yield: 95%) of a fraction having a boiling point of 71 to 73° C./29 mmHg.

The product was identified to be 4-methyl-2-oxetanone by gas chromatography, and its absolute configuration was confirmed to be an (S)-form from the specific rotation $[\alpha]_D^{25} = -24°$ (c=5.9, CHCl$_3$).

The product was subjected to solvolysis in methanol and then led to a methoxytrifluoromethylphenylacetic acid ester, which was analyzed by H-NMR. From the ratio of measured values of diastereomers, the optical purity of the product was found to be 90% e.e.

EXAMPLE 2

In a 100 ml-volume stainless steel autoclave was charged 17.1 mg (0 01 mmol) of Ru$_2$Cl$_4$((−)-Tol-BINAP)$_2$NEt$_3$, and 10 ml of methylene chloride was added thereto to dissolve. To the solution was added 2.42 mg (0.02 mmol) of dimethylaniline, followed by stirring at 50° C. for 20 minutes. To the mixture was added 1.7 g (20 mmol) of 4-methylene-2-oxetanone, followed by stirring at 60° C. and a hydrogen pressure of 100 kg/cm² for 60 hours.

The reaction mixture was distilled in the same manner as in Example 1 to obtain 1.64 g (percent yield: 95%) of (R)-4-methyl-2-oxetanone. The optical purity of the product was 91% e.e. as determined in the same manner as in Example 1.

EXAMPLE 3

In a 100 ml-volume stainless steel autoclave was charged 15.3 mg (0.01 mmol) of $Ru_2Cl_4((+)\text{-}BIPHEMP)_2NEt_3$, and 10 ml of tetrahydrofuran was added thereto to dissolve. To the solution was added 2.6 mg (0.02 mmol) of diisopropylethylamine, followed by stirring at 50° C. for 20 minutes. To the mixture was added 1.7 g (20 mmol) of 4-methylene-2-oxetanone, followed by stirring at 50° C. and a hydrogen pressure of 100 kg/cm² for 56 hours.

The reaction mixture was distilled in the same manner as in Example 1 to obtain 1.56 g (percent yield: 90%) of (S)-4-methyl-2-oxetanone. The optical purity of the product was 89% e.e. as determined in the same manner as in Example 1.

EXAMPLE 4

In a 100 ml-volume stainless steel autoclave was charged 22 mg (0.02 mmol) of $[RuI(p\text{-cymene})((+)\text{-}BINAP)]I$, and 10 ml of methylene chloride was added thereto to dissolve. To the solution was added 2.6 mg (0.02 mmol) of diisopropylethylamine, followed by stirring at 50° C. for 20 minutes. To the mixture was added 1.7 g (20 mmol) of 4-methylene-2-oxetanone, followed by stirring at 50° C. and a hydrogen pressure of 80 kg/cm² for 50 hours.

The reaction mixture was distilled in the same manner as in Example 1 to obtain 1.6 g (percent yield: 93%) of (S)-4-methyl-2-oxetanone. The optical purity of the product was 89% e.e. as determined in the same manner as in Example 1.

EXAMPLE 5

In a 100 ml-volume stainless steel autoclave was charged 13.98 mg (0.02 mmol) of $[RuCl(benzene)((+)\text{-}BIPHEMP)]Cl$, and 10 ml of ethyl acetate was added thereto to dissolve. To the solution was added 2.6 mg (0.02 mmol) of diisopropylethylamine, followed by stirring at 50° C. for 20 minutes. To the mixture was added 1.7 g (20 mmol) of 4-methylene-2-oxetanone, followed by stirring at 50° C. and a hydrogen pressure of 100 kg/cm² for 50 hours.

The reaction mixture was distilled in the same manner as in Example 1 to obtain 1.6 g (percent yield: 93%) of (S)-4-methyl-2-oxetanone. The optical purity of the product was 90% e.e. as determined in the same manner as in Example 1.

EXAMPLE 6

In a 100 ml-volume stainless steel autoclave was charged 20.78 mg (0.02 mmol) of $[RuI(p\text{-cymene})((-)\text{-}BIPHEMP)]I$, and 10 ml of methylene chloride was added thereto to dissolve. To the solution was added 2.6 mg (0.02 mmol) of diisopropylethylamine, followed by stirring at 50° C. for 20 minutes. To the mixture was added 1.7 g (20 mmol) of 4-methylene-2-oxetanone, followed by stirring at 50° C. and a hydrogen pressure of 90 kg/cm² for 45 hours.

The reaction mixture was distilled in the same manner as in Example 1 to obtain 1.64 g (percent yield: 95%) of (R)-4-methyl-2-oxetanone. The optical purity of the product was 90% e.e. as determined in the same manner as in Example 1.

EXAMPLE 7

In a 100 ml-volume stainless steel autoclave was charged 17.7 mg (0.02 mmol) of $Ru((-)\text{-BINAP})Br_2$, and 10 ml of tetrahydrofuran was added thereto to dissolve. To the solution was added 1.3 mg (0.01 mmol) of diisopropylethylamine, followed by stirring at 50° C. for 20 minutes. To the mixture was added 1.7 g (20 mmol) of 4-methylene-2-oxetanone, followed by stirring at 55° C. and a hydrogen pressure of 100 kg/cm² for 50 hours.

The reaction mixture was distilled in the same manner as in Example 1 to obtain 1.59 g (percent yield: 92%) of (R)-4-methyl-2-oxetanone. The optical purity of the product was 91% e.e. as determined in the same manner as in Example 1.

EXAMPLE 8

In a 50 ml-volume egg-plant flask with a three way stop-cock was charged 16.8 mg (0.02 mmol) of $Ru((+)\text{-}BINAP)(O_2CCH_3)_2$, and 10 ml of methylene chloride was added thereto to dissolve. To the solution was added a 15% hydrochloric acid aqueous solution in such an amount to give 2 mols of hydrochloric acid per mol of the complex, followed by stirring at room temperature for 20 minutes. The methylene chloride was removed by distillation under reduced pressure (20 mmHg), and the residue was dried in high vacuo (0.1 mmHg) at room temperature for 2 hours. The residue was transferred to a 100 ml-volume stainless steel autoclave, and 20 ml of tetrahydrofuran and 2 mg (0.02 mmol) of triethylamine were added thereto, followed by stirring at 50° C. for 10 minutes. Finally, 1.7 g (20 mmol) of 4-methylene-2-oxetanone was added, and the mixture was stirred at 50° C. and a hydrogen pressure of 100 kg/cm² for 45 hours.

The reaction mixture was distilled in the same manner as in Example 1 to obtain 1.6 g (percent yield: 93%) of (S)-4-methyl-2-oxetanone. The optical purity of the product was 90% e.e. as determined in the same manner as in Example 1.

EXAMPLE 9

In a 50 ml-volume egg-plant flask with a three way stop-cock was charged 17.94 mg (0.02 mmol) of $Ru((-)\text{-Tol-BINAP})(O_2CCH_3)_2$, and 10 ml of methylene chloride was added thereto to dissolve. To the solution was added a 20% hydrobromic acid aqueous solution in such an amount to give 2 mols of hydrobromic acid per mol of the complex, followed by stirring at room temperature for 30 minutes. The methylene chloride was removed by distillation under reduced pressure (20 mmHg), and the residue was dried in high vacuo (0.1 mmHg) at room temperature for 2 hours. The residue was transferred to a 100 ml-volume stainless steel autoclave, and 10 ml of 1,4-dioxane and 2 mg (0.02 mmol) of triethylamine were added thereto, followed by stirring at 50° C. for 1 hour. Finally, 0.85 g (10 mmol) of 4-methylene-2-oxetanone was added, and the mixture was stirred at 50° C. and a hydrogen pressure of 100 kg/cm² for 20 hours.

The reaction mixture was distilled in the same manner as in Example 1 to obtain 0.83 g (percent yield: 97%) of (R)-4-methyl-2-oxetanone. The optical purity of the product was 89% e.e. as determined in the same manner as in Example 1.

EXAMPLES 10 TO 20

Optically active 4-methyl-2-oxetanone was prepared in the same manner as in Example 6, except for using each of the ruthenium-optically active phosphine complexes shown in Table 1 below. In Examples 19 and 20, before addition of the starting 4-methylene-2-oxetanone, a 20% hydrobromic acid aqueous solution was added to the reaction system in such an amount to give 4 mols of hydrobromic acid per mol of the complex, the mixture was dried under reduced pressure (1 mmHg) at 40° C., and then the starting compound and a solvent were added thereto to conduct the reaction. The reaction results are also shown in Table 1.

TABLE 1

| Example No. | Ruthenium-Optically Active Phosphine Complex | Percent Yield (%) | Optical Purity (% e.e.) | Absolute Configuration |
|---|---|---|---|---|
| 10 | $Ru_2Cl_4((-)\text{-Methoxy-BINAP})_2NEt_3$ | 93 | 85 | (R) |
| 11 | $Ru_2Cl_4((-)\text{-3,5-dimethyl-BINAP})_2NEt_3$ | 75 | 78 | (R) |
| 12 | $RuHCl((+)\text{-BINAP})_2$ | 68 | 65 | (S) |
| 13 | $[Ru((-)\text{-Tol-BINAP})](PF_6)_2$ | 78 | 88 | (R) |
| 14 | $[Ru((-)\text{-BINAP})](BF_4)_2$ | 91 | 89 | (R) |
| 15 | $[RuH((+)\text{-BIPHEMP})_2]ClO_4$ | 69 | 87 | (S) |
| 16 | $[RuCl(benzene)((-)\text{-BINAP})]BPh_4$ | 85 | 89 | (R) |
| 17 | $[Ru(acetonitrile)_4((-)\text{-BINAP})](BF_4)_2$ | 69 | 90 | (R) |
| 18 | $Ru((+)\text{-BINAP})(CF_3CO_2)_2$ | 75 | 83 | (S) |
| 19 | $Ru(C_3H_5)_2((-)\text{-BINAP})$ | 80 | 87 | (R) |
| 20 | $Ru(C_4H_7)_2((-)\text{-BINAP})$ | 85 | 87 | (R) |

EXAMPLE 21

According to the following process, a ruthenium-optically active phosphine complex was prepared by mixing ruthenium with an optically active phosphine in a molar ratio of 1:1, and then an optically active 4-methyl-2-oxetanone was prepared by using the ruthenium-optically active phosphine complex.

Preparation of Ruthenium-Optically Active Phosphine Complex (1:1 by mol)

In 1500 ml of toluene were refluxed 30 g (0.107 mol) of $RuCl_2(COD)$, 72.7 g (0.107 mol) of (−)-Tol-BINAP and 43.3 g (0.428 mol) of triethylamine under heating for 39 hours. After the reaction was over, toluene and the excess triethylamine were distilled under reduced pressure, and the thus precipitated solid matter was dissolved in methylene chloride.

Then, the solution was introduced into Schlenk's tube, and after distilling off methylene chloride, it was dried under reduced pressure at 60° C. to obtain 102.7 g of $Ru_2Cl_4((-)\text{-Tol-BINAP})_2NEt_3$ (theoretical yield: 96.52 g).

Preparation of Optically Active 4-Methyl-2-Oxetanone

In a 30 liter-volume stainless steel-made autoclave previously displaced with a nitrogen gas were placed 2290 g (27.2 mol) of 4-methylene-2-oxetanone previously distilled under a nitrogen gas and 18 liter of dry tetrahydrofuran. Then, a solution of 51.57 g (28.6 mmol) of the above obtained $Ru_2Cl_4((-)\text{-BINAP})_2NEt_3$ dissolved in 500 ml of dry tetrahydrofuran was added thereto, followed by stirring at 50° C. under a hydrogen pressure of 30 kg/cm² for 88 hours. After the completion of reaction, the thus obtained reacting solution was taken out for sampling. As the result of analyzing the product by gas chromatography, it was confirmed that the product had 93.8 % of conversion and 98.3 % of selectivity. Subsequently, tetrahydrofuran was distilled off to obtain 1856 g of a crude (R)-4-methyl-2-oxetanone (purity: 92.3 %; percent yield: 73.1 %; optical purity: 92.3 % ee).

In 1500 ml of ethyl acetate was dissolved 308.1 g of the crude (R)-4-methyl-2-oxetanone obtained above. To the solution were added 300 ml of water and 88 ml of triethylamine, followed by stirring at room temperature for 20 minutes. After allowing the mixture to stand for a while, the organic layer was separated. Then, the solvent was distilled, followed by distillation twice under reduced pressure in the presence of calcium hydride to obtain 180.75 g of a purified (R)-4-methyl-2-oxetanone (percent yield: 65.1%; optical purity: 92 % ee).

EXAMPLE 22

According to the process of Example 21, a ruthenium-optically active phosphine complex was prepared by mixing ruthenium with an optically active phosphine in a molar ratio of 1:1.2, and then an optically active 4-methyl-2-oxetanone was prepared by using the ruthenium-optically active phosphine complex.

That is, in a 500 ml-volume stainless steel-made autoclave previously displaced with a nitrogen gas were placed 54.5 g (0.65 mol) of 4-methylene-2-oxetanone previously distilled under a nitrogen gas and 250 ml of dry tetrahydrofuran. Then, a solution of 1.1685 g (0.65 mmol) of the prepared $Ru_2Cl_4((-)\text{-BINAP})_2NEt_3$ (1:1.2 by mol) dissolved in 50 ml of dry tetrahydrofuran was added thereto, followed by stirring at 50° C. under a hydrogen pressure of 30 kg/cm² for 74 hours.

After the completion of reaction, the thus obtained reacting solution was taken out for sampling. As the result of analyzing the product by gas chromatography, it was confirmed that the product had 98.8% of conversion and 51.3% of selectivity. Subsequently, tetrahydrofuran was distilled off to obtain 28.2 g of a crude (R)-4-methyl-2-oxetanone (percent yield: 50.4%).

The crude (R)-4-methyl-2-oxetanone was dissolved in ethyl acetate in the same manner as in Example 21, followed by adding thereto water and triethylamine and then stirring at room temperature for 20 minutes. After allowing the mixture to stand for a while, the organic layer was separated. Then, the solvent was distilled, followed by distillation twice under reduced pressure in the presence of calcium hydride to obtain 9.5 g of a purified (R)-4-methyl-2-oxetanone (percent yield: 17.0%; optical purity: 92% ee).

Although this Example was conducted in a small reaction scale as compared with Example 21 by reducing the amounts of the reaction compounds, the reaction conditions, e.g., the amount of the catalyst to the starting compound, the solvent, the reaction temperature, the reaction time, the hydrogen pressure, etc., were the same as in Example 21 except that the molar ratio of the ruthenium to the optically active phosphine was changed. Nevertheless, the yield of the product was very low as compared with that of Example 21.

As is apparent from the results, in the process of the present invention, the molar ratio of the ruthenium to the optically active phosphine to be used for the preparation of the ruthenium-optically active phosphine complex catalyst is also an important factor, and the complex prepared by mixing ruthenium with an optically active phosphine in a molar ratio of about 1:1 can provide the desired optically active 4-methyl-2-oxetanone in a high yield.

EXAMPLE 23

According to the process of Example 21, $Ru_2Cl_4(m\text{-}Tol\text{-}BINAP)_2NEt_3$ was prepared by mixing ruthenium with an optically active phosphine in a molar ratio of 1:1, and then 4-methylene-2-oxetanone was subjected to asymmetical hydrogenation by using the above obtained ruthenium-optically active phosphine complex to produce an optically active 4-methyl-2-oxetanone.

EXAMPLE 24

According to the process of Example 21, $Ru_2Cl_4(CyBINAP)_2NEt_3$ was prepared by mixing ruthenium with an optically active phosphine in a molar ratio of 1:1, and then 4-methylene-2-oxetanone was subjected to asymmetrical hydrogenation by using the above obtained ruthenium-optically active phosphine complex to produce an optically active 4-methyl-2-oxetanone.

EXAMPLE 25

According to the process of Example 21, $Ru_2Cl_4(C\text{-}pBINAP)_2NEt_3$ was prepared by mixing ruthenium with an optically active phosphine in a molar ratio of 1:1, and then 4-methylene-2-oxetanone was subjected to asymmetrical hydrogenation by using the above obtained ruthenium-optically active phosphine complex to produce an optically active 4-methyl-2-oxetanone.

EXAMPLE 26

According to the process of Example 21, $Ru_2Cl_4(BICHEP)_2NEt_3$ was prepared by mixing ruthenium with an optically active phosphine in a molar ratio of 1:1, and then 4-methylene-2-oxetanone was subjected to asymmetrical hydrogenation by using the above obtained ruthenium-optically active phosphine complex to produce an optically active 4-methyl-2-oxetanone.

EXAMPLE 27

According to the process of Example 21, $Ru_2Cl_4(OcHBINAP)_2NEt_3$ was prepared by mixing ruthenium with an optically active phosphine in a molar ratio of 1:1, and then 4-methylene-2-oxetanone was subjected to asymmetrical hydrogenation by using the above obtained ruthenium-optically active phosphine complex to produce an optically active 4-methyl-2-oxetanone.

According to the process of the present invention, optically active 4-methyl-2-oxetanone of high optical purity can be obtained easily and economically.

While the invention has been described in detail and with reference to specific examples thereof, it will be apparent to one skilled in the art that various changes and modifications can be made therein without departing from the spirit and scope thereof.

What is claimed is:

1. A process for preparing optically active 4-methyl-2-oxetanone which comprises asymmetrically hydrogenating 4-methylene-2-oxetanone in the presence of a ruthenium-optically active phosphine complex.

2. The process as claimed in claim 1, wherein the ruthenium-optically active phosphine complex is prepared by mixing ruthenium with an optically active phosphine in a molar ratio of from 1:1 to 1:0.95.

3. The process as claimed in claim 1, wherein the asymmetric hydrogenation is carried out in the co-presence of a tertiary amine.

4. The process as claimed in claim 2, wherein the asymmetric hydrogenation is carried out in the co-presence of a tertiary amine.

5. The process as claimed in claim 1, wherein the ruthenium-optically active phosphine complex is selected from the group consisting of the following compounds (1) to (5):

(1) $Ru_xH_yCl_z(CBP)_2(A)_w$ wherein CBP represents $R^1$-BINAP or BIPHEP, wherein $R^1$-BINAP represents a tertiary phosphine represented by formula:

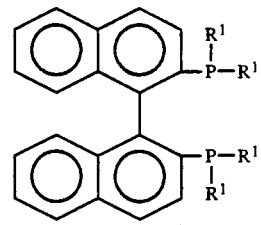

wherein $R^1$ represents an aryl group or a cycloalkyl group having from 3 to 8 carbon atoms; and
BIPHEP represents a tertiary phosphine represented by formula:

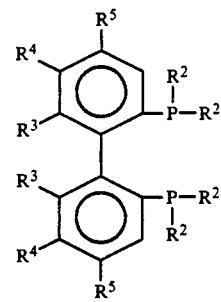

wherein $R^2$ represents an aryl group or a cyclohexyl group; $R^3$ represents a methyl group or a methoxy group; $R^4$ represents a hydrogen atom, a methyl group or a methoxy group; $R^5$ represents a hydrogen atom, a methyl group, a methoxy group or a di-lower alkyl-substituted amino group; and $R^3$, $R^4$ and their adjacent phenyl group may together form an octahydronaphthyl group;

A represents a tertiary amine; y represents 0 or 1; when y is 0, x is 2, z is 4, and w is 1; and when y is 1, x is 1, z is 1, and w is 0;

(2) $[RuH_m(CBP)_n]T_p$ wherein CBP is as defined above; T represents $ClO_4$, $BF_4$, or $PF_6$; when m is 0, n represents 1, and p represents 2; and when m is 1, n represents 2, and p represents 1;

(3) $[RuX_a(Q)_b(CBP)]L_c$ wherein CBP is as defined above; X represents a halogen atom; Q represents substituted or unsubstituted benzene or acetonitrile; L represents a halogen atom, $ClO_4$, $PF_6$, $BF_4$ or $BPh_4$ (wherein Ph represents a phenyl group); when Q is substituted or unsubstituted benzene, a, b, and c each represent 1; when Q is acetonitrile, a is 0, b is 4, and c is 2, or a is 1, b is 2, and c is 1; and when Q is p-cymene which is a substituted benzene and X and L both are an iodine atom, a is 1, b is 1, and c is 1 or 3;

(4) $Ru(CBP)J_2$ wherein CBP is as defined above; and J represents a chlorine atom, a bromine atom or $O_2CR^6$, wherein $R^6$ represents a lower alkyl group or a halogen-substituted lower alkyl group; and (5) $RuG_2(CBP)$ wherein CBP is as defined above; and G represents an allyl group or a methallyl group.

6. The process as claimed in claim 2, wherein the ruthenium-optically active phosphine complex is selected from the group consisting of the following compounds (1) to (5):

(1) $Ru_xH_yCl_z(CBP)_2(A)_w$ wherein CBP represents $R^1$-BINAP or BIPHEP, wherein $R^1$-BINAP represents a tertiary phosphine represented by formula:

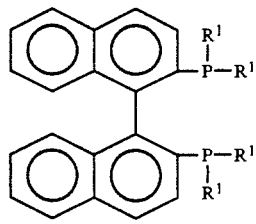

wherein $R^1$ represents an aryl group or a cycloalkyl group having from 3 to 8 carbon atoms; and BIPHEP represents a tertiary phosphine represented by formula:

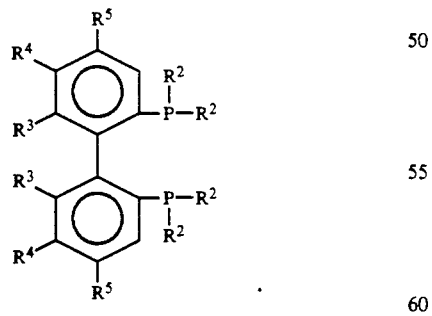

wherein $R^2$ represents an aryl group or a cyclohexyl group; $R^3$ represents a methyl group or a methoxy group; $R^4$ represents a hydrogen atom, a methyl group or a methoxy group; $R^5$ represents a hydrogen atom, a methyl group, a methoxy group or a di-lower alkyl-substituted amino group; and $R^3$, $R^4$ and their adjacent phenyl group may together form an octahydronaphthyl group;

A represents a tertiary amine; y represents 0 or 1; when y is 0, x is 2, z is 4, and w is 1; and when y is 1, x is 1, z is 1, and w is 0;

(2) $[RuH_m(CBP)_n]T_p$ wherein CBP is as defined above; T represents $ClO_4$, $BF_4$, or $PF_6$; when m is 0, n represents 1, and p represents 2; and when m is 1, n represents 2, and p represents 1;

(3) $[RuX_a(Q)_b(CBP)]L_c$ wherein CBP is as defined above; X represents a halogen atom; Q represents substituted or unsubstituted benzene or acetonitrile; L represents a halogen atom, $ClO_4$, $PF_6$, $BF_4$ or $BPh_4$ (wherein Ph represents a phenyl group); when Q is substituted or unsubstituted benzene, a, b, and c each represent 1; when Q is acetonitrile, a is 0, b is 4, and c is 2, or a is 1, b is 2, and c is 1; and when Q is p-cymene which is a substituted benzene and X and L both are an iodine atom, a is 1, b is 1, and c is 1 or 3;

(4) $Ru(CBP)J_2$ wherein CBP is as defined above; and J represents a chlorine atom, a bromine atom or $O_2CR^6$, wherein $R^6$ represents a lower alkyl group or a halogen-substituted lower alkyl group; and (5) $RuG_2(CBP)$ wherein CBP is as defined above; and G represents an allyl group or a methallyl group.

7. The process as claimed in claim 3, wherein the ruthenium-optically active phosphine complex is selected from the group consisting of the following compounds (1) to (5):

(1) $Ru_xH_yCl_z(CBP)_2(A)_w$ wherein CBP represents $R^1$-BINAP or BIPHEP, wherein $R^1$-BINAP represents a tertiary phosphine represented by formula:

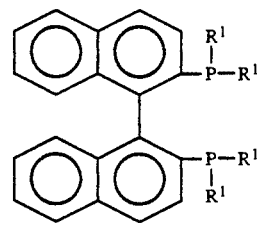

wherein $R^1$ represents an aryl group or a cycloalkyl group having from 3 to 8 carbon atoms; and BIPHEP represents a tertiary phosphine represented by formula:

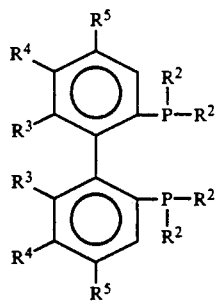

wherein $R^2$ represents an aryl group or a cyclohexyl group; $R^3$ represents a methyl group or a methoxy group; $R^4$ represents a hydrogen atom, a methyl group or a methoxy group; $R^5$ represents a hydrogen atom, a methyl group, a methoxy group or a di-lower alkyl-substituted amino group; and $R^3$, $R^4$ and their adjacent phenyl group may together form an octahydronaphthyl group;

A represents a tertiary amine; y represents 0 or 1; when y is 0, x is 2, z is 4, and w is 1; and when y is 1, x is 1, z is 1, and w is 0;

$[RuH_m(CBP)_n]T_p$ wherein CBP is as defined above; T represents $ClO_4$, $BF_4$, or $PF_6$; when m is 0, n represents 1, and p represents 2; and when m is 1, n represents 2, and p represents 1;

$[RuX_a(Q)_b(CBP)]L_c$ wherein CBP is as defined above; X represents a halogen atom; Q represents substituted or unsubstituted benzene or acetonitrile; L represents a halogen atom, $ClO_4$, $PF_6$, $BF_4$ or $BPh_4$ (wherein Ph represents a phenyl group); when Q is substituted or unsubstituted benzene, a, b, and c each represent 1; when Q is acetonitrile, a is 0, b is 4, and c is 2, or a is 1, b is 2, and c is 1; and when Q is p-cymene which is a substituted benzene and X and L both are an iodine atom, a is 1, b is 1, and c is 1 or 3;

(4) $Ru(CBP)J_2$ wherein CBP is as defined above; and J represents a chlorine atom, a bromine atom or $O_2CR^6$, wherein $R^6$ represents a lower alkyl group or a halogen-substituted lower alkyl group; and (5) $RuG_2(CBP)$ wherein CBP is as defined above; and G represents an allyl group or a methallyl group.

* * * * *